United States Patent [19]

Fishman et al.

[11] Patent Number: 5,313,270
[45] Date of Patent: May 17, 1994

[54] METHOD AND APPARATUS FOR MEASUREMENT OF REFLECTIVITY FOR HIGH QUALITY MIRRORS

[75] Inventors: Ilya M. Fishman; Paul D. Haar, both of Palo Alto, Calif.

[73] Assignee: The Board of Trustees of the Leland Stanford Junior University, Stanford, Calif.

[21] Appl. No.: 879,809

[22] Filed: May 7, 1992

[51] Int. Cl.$^5$ ............................................. G01N 21/55
[52] U.S. Cl. ................................... 356/352; 356/445; 356/448
[58] Field of Search ................. 356/445, 448, 447, 352

[56] References Cited

U.S. PATENT DOCUMENTS

| | | | |
|---|---|---|---|
| 3,679,313 | 7/1972 | Rosenberg | 356/352 |
| 4,436,426 | 3/1984 | Smith | 356/445 |
| 4,448,486 | 5/1984 | Evans | 356/352 |
| 4,571,085 | 2/1986 | Anderson | 356/445 |
| 4,624,573 | 11/1986 | Rahn et al. | 356/445 |
| 4,659,224 | 4/1987 | Monchalin | 356/352 |
| 4,793,709 | 12/1988 | Jabr et al. | 356/445 |
| 5,080,491 | 1/1992 | Monchalin et al. | 356/352 |

FOREIGN PATENT DOCUMENTS

| | | | |
|---|---|---|---|
| 3008252 | 9/1981 | Fed. Rep. of Germany | 356/445 |
| 1316388 | 3/1988 | U.S.S.R. | 356/445 |
| 1509688 | 9/1989 | U.S.S.R. | 356/445 |

OTHER PUBLICATIONS

A. E. Seigman, *Lasers*, 1986, pp. 413–440.
N. A. Vinokurov et al, *Method for measuring reflection coefficients close to unity* (1985).

Primary Examiner—James C. Housel
Assistant Examiner—Laura E. Collins

[57] ABSTRACT

An apparatus and methods are suggested for measuring reflectivity R of highly reflecting coatings, and, in particular, of very high reflectivity $\{(1-R)<0.001\}$ mirrors based on the simultaneous measurement of power reflected from and transmitted through an optical cavity bounded by a mirror of unknown reflectivity and a reference mirror of predetermined reflectivity. To confirm the obtained results the reference mirror is replaced by another mirror of unknown reflectivity manufactured together with the first examined mirror in the same coating run.

30 Claims, 4 Drawing Sheets

METHOD AND APPARATUS FOR MEASUREMENT OF REFLECTIVITY FOR HIGH QUALITY MIRRORS

ORIGIN OF THE INVENTION

The invention described herein was made in the performance of work under ONR Contract No. N00014-91-0170.

FIELD OF THE INVENTION

This invention relates to an apparatus and methods for measuring the reflectivity R of highly reflecting coatings, and, in particular, to an optical system and method for use in making reflection measurements of very high reflectivity $\{(1-R)<0.001\}$ mirrors based on the measurements of power reflected from an optical cavity.

Because of the unique properties of the present invention, it is especially useful for standardization of reflection characteristics of high reflectivity mirrors in a manufacturing processes.

BACKGROUND OF THE INVENTION

The measurement of reflectivities for low loss, highly reflecting coatings needed for mirrors in laser cavities and other optical instruments has been demonstrated over the last decade. It is a problem for mirrors with reflectivities substantially close to unity to determine the mirror's optical properties using conventional measurements such as measurements with Fourier Transform Infrared Spectrometers. To measure high reflectivities, the so-called ring down measurement method has been developed (U.S. Pat. Nos. 4,571,085 and 4,793,709.)

According to the ring down measurement two mirrors with unknown reflectivity are introduced into an optical cavity. An external laser beam is directed into the cavity to accumulate optical energy inside the cavity. Afterward the laser source is turned off abruptly and the stored energy is allowed to decay. Kinetics of the decay determine the total losses of the cavity, and the unknown reflectivity of the mirror is determined as half of the value of measured cavity losses.

If the examined mirror's losses are comparable to the intrinsic cavity losses it becomes impossible to distinguish the mirror losses from the total losses of the cavity, and as a result the definition of the mirror reflectivity becomes unreliable.

Another technique to measure total cavity losses for obtaining the mirror's reflectivity has been disclosed in the U.S. Pat. No. 4,624,573. According to this technique a laser source with harmonically modulated intensity is coupled to an optical cavity which includes a mirror with unknown reflectivity. The total cavity losses are inferred from the phase shift induced on the laser signal while it passes through the cavity. This method, similar to the ring down measurement, obtains the unknown reflectivity of the mirror as half of the value of the total cavity losses. For intrinsic cavity losses compared to mirrors losses, this method experiences the same drawbacks as the ring down measurements.

The method of the present invention and the system for its implementation overcome the disadvantages of the prior art.

It is the object of this invention to provide a method for the measurement of the reflectivity of high quality mirrors.

It is also an object of this invention to provide a method for evaluation of the reflectivity of high quality mirrors.

An additional object of this invention is to provide an apparatus for implementing the aforementioned methods.

SUMMARY OF THE INVENTION

The present invention overcomes the shortcomings of the prior art by providing a novel method of measurement of reflectivity for high quality mirrors based on simultaneous measurements of transmission and reflection from an optical cavity. The first optical cavity is bounded by the examined mirror with unknown reflectivity and the reference mirror with the predetermined reflectivity. The radiation beam generated by a laser source is directed into the optical cavity, and the measurements of transmitted and reflected signals from the cavity are produced. Then the cavity is reconfigured by exchanging positions of the two mirrors, and the same type of measurements are produced for a second constructed cavity as for the first one. Two sets of transmitted and reflected signals allow for the mirrors reflectivity and intrinsic cavity losses to be determined. To confirm the results obtained a third optical cavity is defined by replacing the reference mirror of the second cavity with a mirror of unknown reflectivity manufactured together with the first examined mirror in the same coating run. Subsequently the reflection measurements for the third optical cavity are produced.

For implementation of the disclosed method, a novel apparatus is constructed which comprises a laser source, a telescope for mode matching, a chopper, a beamsplitter, an optical cavity with two mirrors facing each other along their longitudinal axis, a detector for measuring the signal transmitted through the cavity, a detector for measuring the signal reflected from the cavity, an oscilloscope for recording the output signal of the detectors, and a system for aligning the optical cavity.

The novel features of the invention are set forth in the claims of the subject specification. The invention will be best understood from the following detailed disclosure when read in connection with the accompanying drawings.

DESCRIPTION OF PREFERRED EMBODIMENTS

Figure 1:
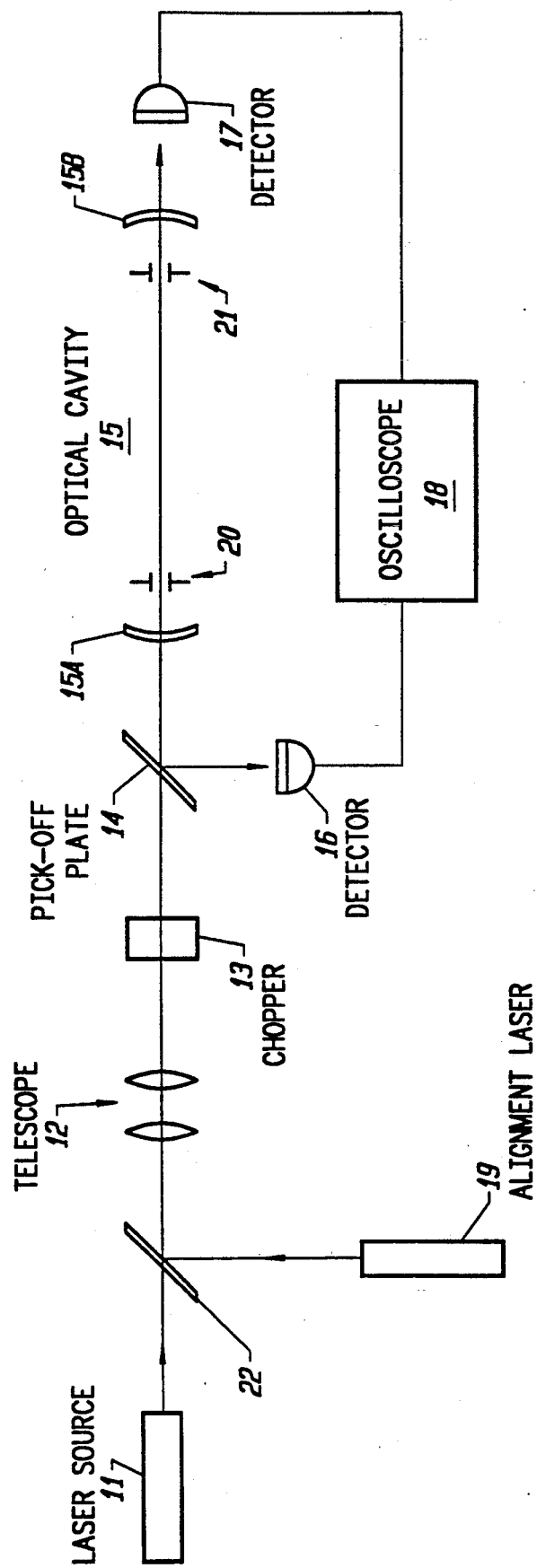
FIG. 1 is a schematic representation of the apparatus for measuring reflected and transmitted signals from an optical cavity.

FIG. 1 illustrates schematically the method and apparatus of the invention. Referring to FIG. 1, a laser beam is projected by a laser source 11 through mode matching telescope 12 and beamsplitter 14 into an optical cavity 15 along its longitudinal axis.

The optical cavity 15 is defined by mirrors 15a and 15b. Mirror 15b is the examined mirror with unknown reflectivity, and mirror 15a is a reference mirror with predetermined reflectivity. The intensity of light passing through the optical cavity 15 is measured by a first detector 17, which is located on the longitudinal axis of the cavity 15 behind mirror 15b, and recorded on an oscilloscope 18. A chopper 13 is placed in the path of laser source 11 in front of the beamsplitter 14 to determine the base line (zero signal) for the reflected signal. The light beam reflected from the front mirror 15a is directed by beamsplitter 14 into a second detector 16 and the intensity of reflected light is recorded on an oscilloscope 18.

For providing the method of measuring reflectivity of examined mirrors, three optical cavities have to be constructed.

Initially, an optical cavity is defined by placing two mirrors 15a and 15b a predetermined distance apart on the longitudinal axis, with their reflecting coatings facing each other. To minimize the intrinsic cavity losses the cavity is aligned using alignment laser source 19 and apertures 20 and 21. Additional beamsplitter 22 placed between the telescope 12 and the laser source 11 deflects a fraction of the alignment laser power in the optical cavity 15. Then, a coherent radiation beam, produced by an appropriate laser source 11, is directed into the cavity 15 along the longitudinal axis. To minimize the radiation losses from the laser source 11 the optical modes of the laser source 11 and the cavity 15 have to be matched. For the mode matching, the position of the lenses of telescope 12 have to be adjusted. Beamsplitter 14 placed between the telescope 12 and the cavity 15, deflects a fraction of power reflected from the cavity, onto the second detector 16.

Measurement of reflection and transmission signals is based on the coherent properties of the laser source 11. Specifically, due to the constructive interference of the radiation as it circulates in the cavity, the optical reflection signal will be less than the reflection from the front mirror 15a. Relationships of the ratios of transmitted signal to the incident power (T) and reflected signal to the incident power (R) are (A. E. Siegman, Lasers, Univ. Sci. Books, 1986):

$$T = \frac{4\delta_1 \delta_2}{(\delta_1 + \delta_2 + \delta_0)^2} \quad (1)$$

$$R = (\sqrt{\delta_1 U} - \sqrt{1 - \delta_1})^2 \quad (2)$$

$$U = \frac{T}{\delta_2}$$

where $\delta_1$ is the losses of the front cavity mirror, $\delta_2$ is the losses of the back cavity mirror, $\delta_0$ the intrinsic losses of the cavity, and U is optical power inside the cavity. Eq.(1) and Eq.(2) are valid close to resonance. If the frequency of the laser source 11 is not in resonance with the cavity, or if the intrinsic cavity losses are very large, then there is no coherent optical power built up inside the cavity. In the latter case, $\delta_0 >> \delta_1, \delta_2$, the transmitted signal is very small, and Eq.(1) yields:

$$T \sim (\delta_1/\delta_0)^2.$$

Far from resonance, reflection from the cavity equals approximately the reflection from the front cavity mirror, $$R \sim (1 - \delta_1)$$

To observe a resonance, the laser source frequency has to be stable and equal to the cavity mode frequency for a considerable time, which is longer than the transient process of the cavity.

Figure 2B:
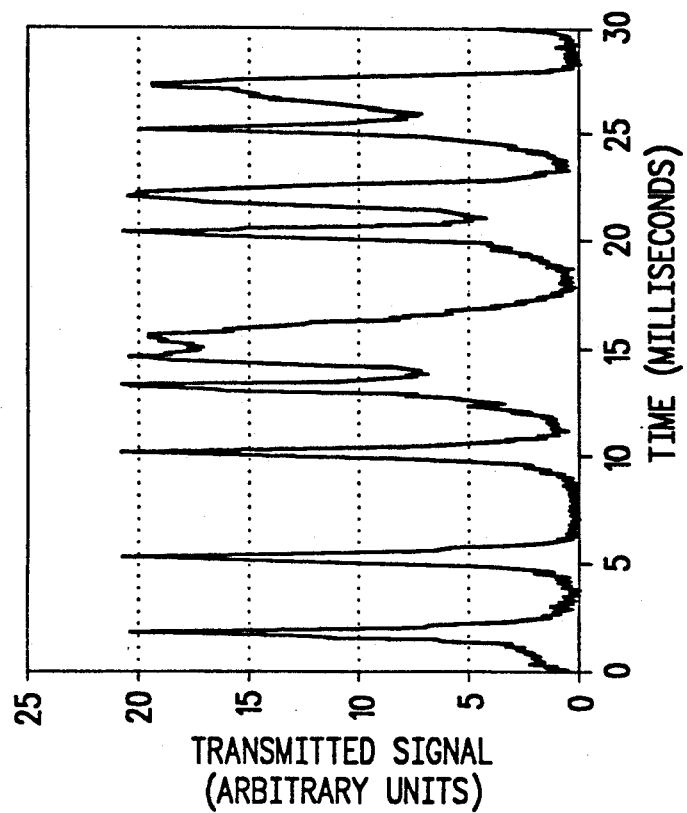
FIG. 2b is an oscillogram of transmitted resonance signal of the optical cavity.
Figure 2A:
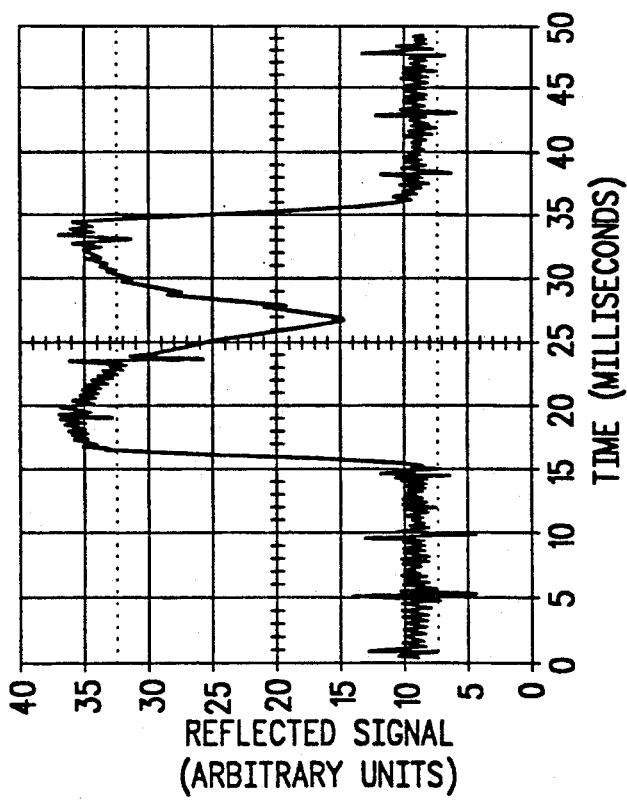
FIG. 2a is an oscillogram of the reflected resonance signal of the optical cavity.

When resonances take place in our measurements we observe short minima of reflected power or peaks of transmitted power on the oscilloscope 18 (FIGS. 2a and 2b). Far from resonance, the reflected signal experiences a maximum, and at the resonance the reflected signal is minimized. The ratio of the minimum to the maximum reflected signal, if both are measured with the same detector, is a relative reflected signal which is independent of detector calibration.

After the measurement of maximum transmitted signal and maximum relative reflected signal, a second optical cavity is constructed by reversing the position of the two mirrors 15a and 15b. To insure that alignment of both cavities is identical, the second optical cavity is aligned to obtain the same value of the optical transmission signal equal to the signal of the first optical cavity. The first detector 17 is used for this measurement. The second detector 16 is then used to measure the second optical reflection signal. The reflectivity of the mirror to be measured can then be determined from the reflectivity of the reference mirror, and the first and second relative reflection signals. Eq. 2 is used to determine two unknown numbers $\delta_0$ and $\delta_2$, with two measured relative reflection signals.

Figure 3:
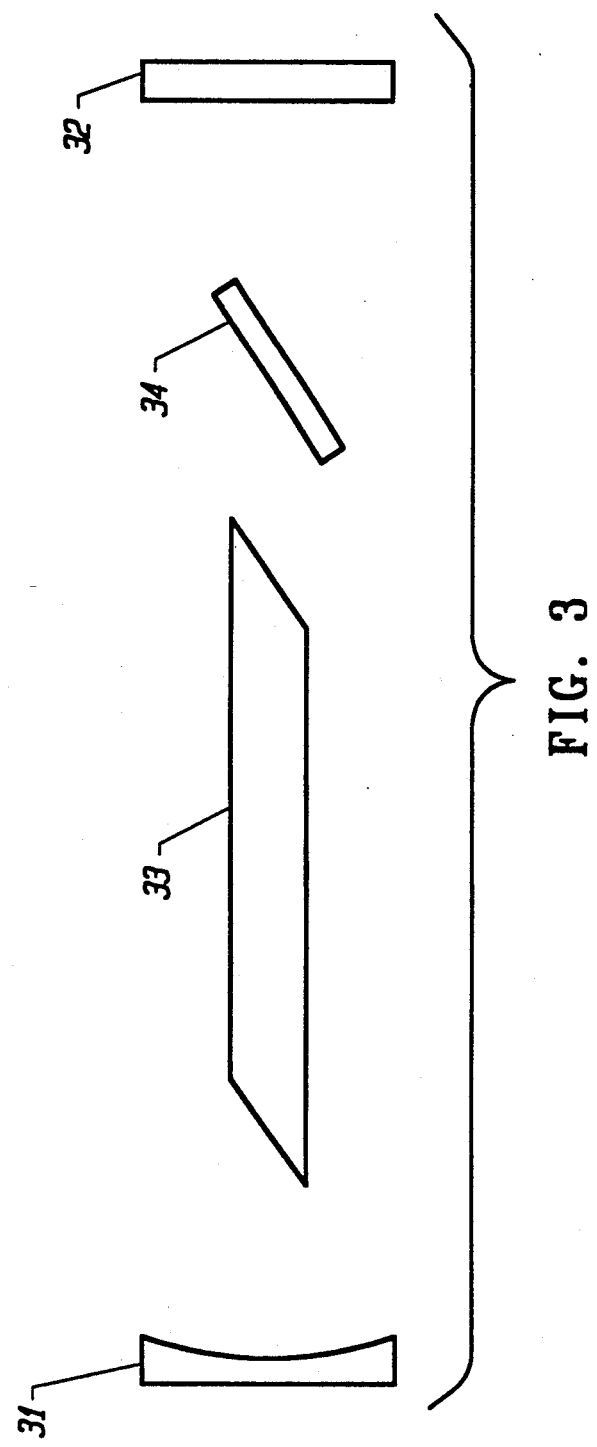
FIG. 3 is a schematic representation of the infrared laser cavity.

The required frequency stability of the laser source is an important attribute, especially for the infrared lasers. We achieved significant frequency stability of our 3.39 micron HeNe laser by introducing inside the cavity a thin (300 micron) Ge flat-flat plate 34 at the Brewster angle to the optical axis (FIG. 3). This plate was intended both to cut the laser tube 33 oscillation in the near infrared spectrum and to separate the cavity longitudinal modes. Beyond that, we substituted for the commercial front cavity mirror having about 30% transmission, a 100% reflector 31 identical to the back cavity mirror 32 to increase the laser amplification. Cavity resonances observed in our experiments resulted from random coincidences of frequencies of the laser source 11 and optical cavity 15. In principle, frequency resonance could be stabilized by using an active feedback loop.

In addition to measuring the mirror's reflectivity the proposed technique allows for separate measurement of the intrinsic cavity losses. Two equations (1) and (2) allow for this measurement for any set of cavity parameters. However, measurement of intrinsic cavity losses is especially important if $\delta_0 >> \delta_2$. Though intrinsic cavity losses comprise the diffraction losses, losses caused by mode mismatch, losses due to mirror fabrication errors, being usually small (~0.1%) are nevertheless crucial for measuring the high reflectivities. The step of defining the intrinsic cavity losses confirms the validity of the reflectivity evaluation.

Figure 4:
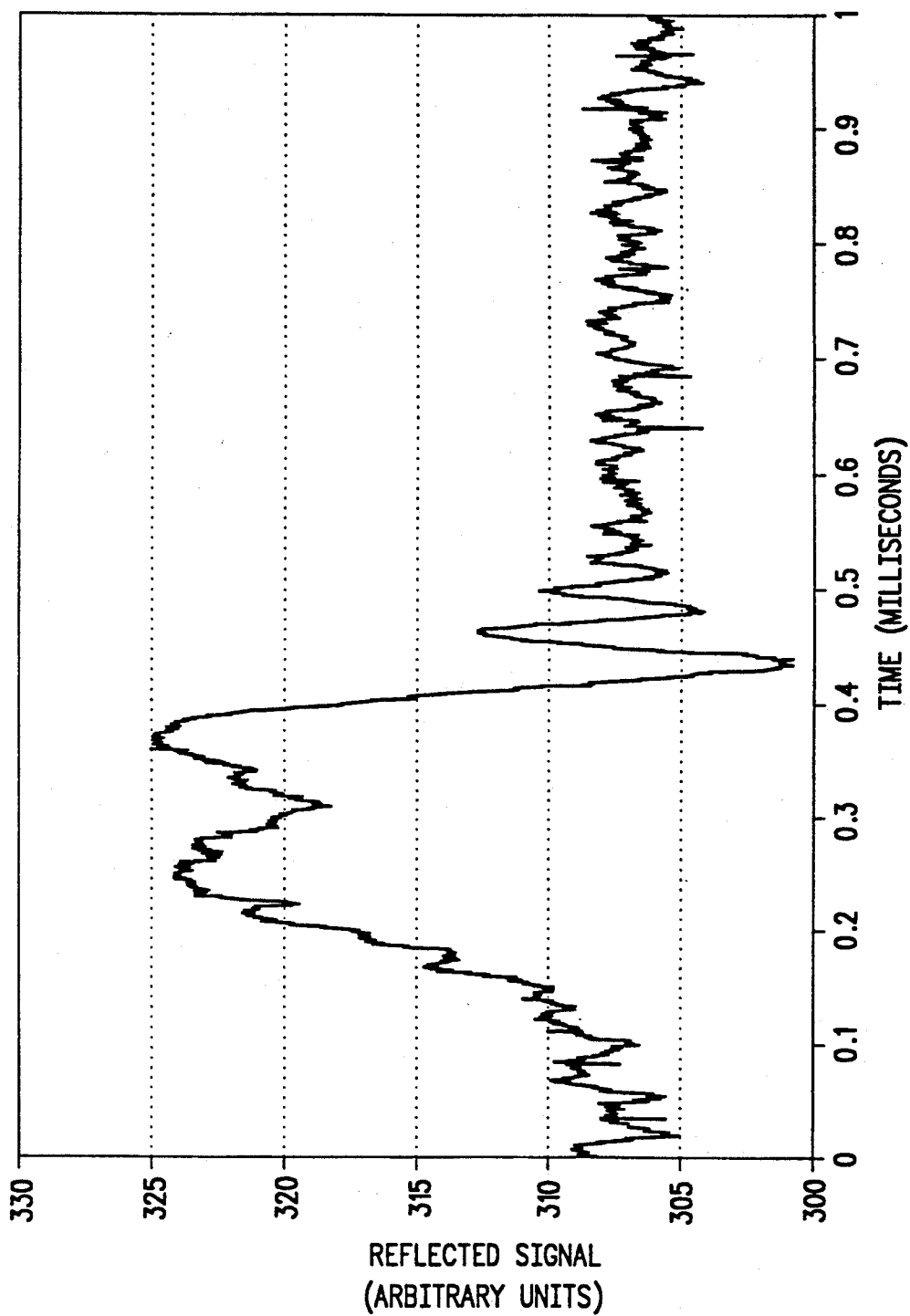
FIG. 4 is a graph of the reflected signal from the optical cavity bounded by two mirrors with unknown reflectivities.

To verify the measured value of the mirror's reflectivity, a third optical cavity is constructed by replacing the reference mirror in the second cavity by a mirror identical to the examined mirror with the mirror of unknown reflectivity manufactured together with the first examined mirror in the same coating run. The third relative reflected signal is measured similar to the relative reflected signal measured in the first optical cavity. The ratio of the intrinsic cavity losses to the losses of one of the mirrors (provided that in this case the mirrors are identical) can then be inferred from this optical reflection signal. This ratio can be used to infer the reflectivity or intrinsic cavity losses if the other is known in advance, or to confirm the reflectivity and intrinsic cavity losses measured earlier. It has to be pointed out that for the third optical cavity, the transmitted signal intensity is very small because of the small ratio of mirror losses to intrinsic cavity losses (see Eq. 1). At the same time, the intensity of the reflected signal is easily detectable because of the interference of the wave reflected from the front mirror and the wave transmitted from the cavity through the same mirror. The shape of the signal reflected from the third optical cavity at resonance is usually complicated by the transient processes. An example of the signal reflected at resonance from the third optical cavity is given at FIG. 4. Damped oscillations of FIG. 4 allow for additional definition of the total cavity losses.

In the apparatus as shown in FIG. 1 for implementing the disclosed method a radiation source 11 for producing a radiation beam of coherent light is a laser, for example LSIR-0100-339M (PMS Electro-Optics). Cavity mirrors 15a and 15b are dielectric coated substrates. For infrared mirrors, ZnSe, CaF$_2$, Si substrates could be used. In our measurements, convexconcave IR mirrors coated for (3-5) micron spectral range on ZnSe substrates are used. The optical cavity 15 is constructed by placing two mirrors 15a and 15b a predetermined distance apart, with their coatings facing each other. The mirrors have to be centered on the longitudinal axis. For proper cavity alignment, mirror mounts pivoted about their centers are preferably used. The alignment system consists of visible alignment laser 19 (FIG. 1) and two apertures placed inside the cavity, symmetric about the center. Two alignment lasers which are directed into the cavity from both ends may be used as an alternative. Laser source 11 must be mode matched into the optical cavity. This is done with the mode matching telescope 12 typically consisting of two lenses (made of ZnSe, CaF$_2$, Si or another infrared material), placed in the path of the laser beam between the laser source and the optical cavity. To provide the high quality mode matching, lenses have to be installed on translation stages allowing for micrometer displacement both along and normal to the optical axis. A beamsplitter 14 placed between the mode matching telescope and the cavity has to deflect the light reflected from the optical cavity onto a detector. A flat-flat plate of infrared material (ZnSe, CaF$_2$ or Si) is used for this purpose. Detector 17 measures the optical reflection signal, and detector 16 measures the optical transmission signal. We used liquid nitrogen cooled InSb detectors J10-M204-R01M, together with PA-6 preamplifiers from EG&G Judson in our apparatus. An oscilloscope 18, such as Tektronix 2225 or, preferably, LeCroy 9410 memory oscilloscope 18 is used to register and store the data. A chopper 13 between the laser source and the cavity alternately blocks the light beam and allows for registration of both the optical transmission and reflection signals and the base line (zeroes) of reflection and transmission. The chopper speed must be set to modulate the beam at a rate slow compared to the time required for the optical transmission and reflection signals to reach the steady state. We used the chopper SRS540 in our measurements.

This invention is not limited to the preffered embodiment heretofore described, to which variations and improvements may be made without departing from the scope of protection of the present invetion the characteristics of which are summarized in the following claims.

We claim:

1. A method for measurement of reflectivity of high quality mirrors comprising the steps of:

defining a first optical cavity by commonly disposing first and second mutually spaced mirrors placed along a longitudinal axis with reflecting surfaces perpendicular to said longitudinal axis and facing each other, said first mirror having predetermined reflectivity;

directing a radiation beam into said first optical cavity along said longitudinal axis, said radiation beam produced by a radiation source and transmitted through a beamsplitter which is interposed between said first optical cavity and said radiation source on said longitudinal axis;

measuring a first optical transmission signal of said first optical cavity by a first detector, said first detector positioned on said longitudinal axis behind said second mirror; measuring a first relative reflection signal of said first optical cavity by a second detector, said second detector located in a deflection plane of said beamsplitter;

forming a second optical cavity by reversing the position of said first and said second mirrors respectively;

aligning said second optical cavity to obtain a second optical transmission signal from said first detector;

measuring a second relative reflection signal of said second optical cavity by said second detector; and determining a reflection coefficient of said second mirror as a function of said predetermined reflectivity and said first and second relative reflection signals.

2. The method of claim 1 wherein the first relative reflection signal is a ratio of minimum to maximum amplitude of a first reflection signal obtained by said second detector.

3. The method of claim 1 wherein the second relative reflection signal is a ratio of minimum to maximum amplitude of a second reflection signal obtained by said second detector.

4. The method of claim 1 wherein said radiation beam source is a laser having frequency stability during at least the observation of said first and second optical reflection signal.

5. The method of claim 4 wherein said frequency stability of said laser is obtained by damping of high frequency fluctuations of said laser.

6. The method of claim 4 wherein said frequency stability of said laser is obtained by controlling said frequency through an active feedback loop.

7. The method of claim 1 wherein said second mirror has a multilayer dielectric coating.

8. A method for evaluation of reflectivity for high quality mirrors comprising the steps of:

defining a first optical cavity by commonly disposing first and second mutually spaced mirrors placed along a longitudinal axis with reflecting surfaces perpendicular to perpendicular said longitudinal axis and facing each other, said first mirror having predetermined reflectivity;

directing a radiation beam into said first optical cavity along said longitudinal axis, said radiation beam produced by a radiation source and transmitted through a beamsplitter which is interposed between said first optical cavity and said radiation source on said longitudinal axis;

measuring a first optical transmission signal of said first optical cavity by a first detector, said first detector positioned on said longitudinal axis behind said second mirror; measuring a first relative reflection signal of said first optical cavity by a second detector, said second detector located in a deflection plane of said beamsplitter;

forming a second optical cavity by reversing the position of said first and said second mirrors respectively;

aligning said second optical cavity to obtain a second optical transmission signal from said first detector;

measuring by said second detector a second relative reflection signal of said second optical cavity;

obtaining intrinsic cavity losses of said first optical cavity from the relationship of said predetermined reflectivity and said first and second relative reflection signals;

determining a reflection coefficient of said second mirror as a function of said predetermined reflectivity and said first and second relative reflection signals; and evaluating reflectivity of said second mirror by comparing said reflection coefficient with said intrinsic cavity losses.

9. The method of claim 8 wherein the first relative reflection signal is a ratio of minimum to maximum amplitude of a first reflection signal obtained by said second detector.

10. The method of claim 8 wherein the second relative reflection signal is a ratio of minimum to maximum amplitude of a second reflection signal obtained by said second detector.

11. The method of claim 8 wherein said radiation beam source is a laser having sufficient frequency stability during at least the observation of said first and second optical reflection signal.

12. The method of claim 11 wherein said frequency stability of said laser is obtained by damping of high frequency fluctuations of said laser.

13. The method of claim 11 wherein said frequency stability of said laser is obtained by controlling said frequency through an active feedback loop.

14. The method of claim 8 wherein said second mirror comprises a multilayer dielectric coating.

15. A method of verification of reflectivity measurement for high quality mirrors comprising the steps of:
defining a first optical cavity by commonly disposing first and second mutually spaced mirrors placed along a longitudinal axis with reflecting surfaces perpendicular to said longitudinal axis and facing each other, said first mirror having predetermined reflectivity;

directing a radiation beam into said first optical cavity along said longitudinal axis, said radiation beam produced by a radiation source and transmitted through a beamsplitter which is interposed between said first optical cavity and said radiation source on said longitudinal axis;

measuring a first optical transmission signal of said first optical cavity by a first detector, said first detector positioned on said longitudinal axis behind said second mirror;

measuring a first relative refection signal of said first optical cavity by said second detector, said second detector located in a deflection plane of said beamsplitter;

forming a second optical cavity by reversing the position of said first and said second mirrors respectively;

aligning said second optical cavity to obtain a second optical transmission signal from said first detector;

measuring by a second detector a second relative reflection signal of said second optical cavity;

determining a reflection coefficient of said second mirror as a function of said predetermined reflectivity and said first and second relative reflection signals;

forming a third optical cavity from said second optical cavity by substituting a third mirror in place of said first mirror, said third mirror having a reflection coefficient substantially equal to the reflection coefficient of said second mirror;

aligning said third optical cavity by adjusting said third mirror to maximize the signal of said first detector;

measuring a third relative reflection signal of said third optical cavity by a second detector; and comparing said reflection coefficient of said second mirror by matching it with a reflection coefficient of said third mirror.

16. The method of claim 15 wherein the first relative reflection signal is a ratio of minimum to maximum amplitude of a first reflection signal obtained by said second detector.

17. The method of claim 15 wherein said second relative reflection signal is a ratio of minimum to maximum amplitudes of a second reflection signal obtained by said second detector.

18. The method of claim 15 wherein said radiation beam source is a laser having frequency stability during at least the observation of said first and second optical reflection signal.

19. The method of claim 18 wherein said frequency stability of said laser is obtained by damping of high frequency fluctuations of said laser.

20. The method of claim 18 wherein said frequency stability of said laser is obtained by controlling said frequency through an active feed back loop.

21. The method of claim 15 wherein said second mirror comprises a multilayer dielectric coating.

22. The method of claim 15 wherein said reflection coefficient of said second mirror is defined with respect to cavity losses of said third optical cavity.

23. The method of claim 15 wherein said second and said third mirrors have identical coating characteristics.

24. Apparatus for measurement of reflectivity for high quality mirrors comprising:
a radiation source for producing a radiation beam of coherent light;
an optical cavity bounded by a pair of mirrors on a longitudinal axis, said pair of mirrors spaced apart and displaceable with respect to one another;
means for alignment of said optical cavity;
means for mode matching of said radiation source and said optical cavity, said mode matching means placed between said radiation source and said optical cavity on said longitudinal axis;

a beamsplitter for permeating a radiation beam from said radiation source to permeate said optical cavity and deflecting a reflected beam, said beamsplitter interposed between said radiation source and said optical cavity on said longitudinal axis;

a first detector for measuring optical transmission signals from said optical cavity, said optical cavity disposed between said beamsplitter and said first detector on said longitudinal axis;

a second detector for measuring optical reflection signals from said optical cavity deflected by said beamsplitter, said second detector disposed in the deflection plane of said beamsplitter; and means for registration of said optical transmission and reflection signals from said first and second detectors, said first and second detectors electrically connected to said means for registration.

25. The apparatus of claim 24 wherein said radiation source consists of a laser cavity formed by two laser mirrors with a filter, a laser tube and a spacer disposed therebetween on a laser cavity axis.

26. The apparatus of claim 25 wherein said two mirrors have reflectivity substantially close to unity.

27. The apparatus of claim 24 further comprising means for zero setting of said second detector.

28. The apparatus of claim 27 wherein said means for zero setting of said second detector is a chopper.

29. The apparatus of claim 24 wherein said means for alignment of said optical cavity includes:

a pick-off plate disposed outside said optical cavity on the longitudinal axis between said radiation source and said first detector;

an alignment laser positioned in a deflection plane of said pick-off plate;

a pair of spaced apart alignment apertures placed inside said optical cavity on said longitudinal axis.

30. The apparatus of claim 29 wherein said alignment laser has a wavelength range within the visible spectrum.

* * * * *